United States Patent [19]
Monis et al.

[11] Patent Number: 5,965,355
[45] Date of Patent: Oct. 12, 1999

[54] ANTIBODIES AND PROTEINS USEFUL FOR ASSAYING VIRUS INFECTION IN GRAPE PLANTS

[75] Inventors: Judit Monis, Beaverton; Richard K. Bestwick, Portland, both of Oreg.

[73] Assignee: Agritope, Inc., Portland, Oreg.

[21] Appl. No.: 08/708,591

[22] Filed: Sep. 5, 1996

Related U.S. Application Data

[60] Provisional application No. 60/004,087, Sep. 21, 1995, and provisional application No. 60/019,916, Jun. 14, 1996.

[51] Int. Cl.$^6$ .............. C12Q 1/70; G01N 33/53; C12N 5/00; C07K 16/00
[52] U.S. Cl. .............. 435/5; 435/7.1; 435/240.1; 530/388.3; 530/388.5; 530/826
[58] Field of Search .............. 435/5, 7.1, 240.1; 530/388.3, 388.5, 826

[56] References Cited

PUBLICATIONS

Boscia et al., *Vitis* 34(3):171–175 (1995).
Boscia et al. (1990) *Phytopathology* 80:117.
Choueiri et al. *Vitis*, 35(2):91–93 (1996).
Gugerli et al. (1984) *Rev Suisse Vitic. Arbotic. Hortic.* 16:299–304.
Gugerli, P. and Ramel, M–E (1993) Extended Abstracts, 11th Meeting of the International Council for the Study of Viruses and Virus Diseases of the Grapvine, pp. 23–24.
Hu et al. (1990) *J. Phytopathology* 128:1–14.
Hu et al. (1990) *Phytopathology* 80:920–925.
Monis, Judit et al. Abstract (1997) *Plant. Dis.* 81:802–808.
Mullins et al., *Biology of the Grapevine*, Cambridge (1994).
Namba et al. (1991) *Phytopathology* 81:964–970.
"U.C. Davis Grapevine Virus Collection" (see Golino, D.A., (1992) *Am. J. Enol. Vitic.*, 43:200–205); the Foundation Plant Material Service (FPMS) at the University of California, Davis, California.
Zee et al. (1987) *Phytopathology* 77, 1427–1434.
Zimmerman et al. (1990) *J. Phytopathology* 130, 205–218.
Landresse, "Clorella Viruses", In:Encyclopedia of Virology vol. 1, Webster & Granoff eds., Academic Press, Harcourt Brace & Co. Publishers, New York, 1994, pp. 242–248.
Hu et al. Phytopathology 80:920–925, 1990.
Boscia et al. Phytopathology 80(1):117, 1990.
Pollini et al. J. Virol. Methods 429(1):107–116, 1993.
Golino, D.A. Am. J. Enol. Vitic., 43:200–205, 1992.
Gugerli et al. "Etiological Studies & Diagnostic of Grapevine Leafroll Disease Improved by Monoclonal Antibodies", In:Monoclonal Antibodies Magniculture: proceedings of the symposium "Perspectives for monoclonal antibodies in agriculture" Laboratory for Monoclonal Antibodies Wageningen, Netherlands, May 30, 1990 A. Schuts ed. pp. 47–54.

*Primary Examiner*—Frank C. Eisenschenk
*Assistant Examiner*—Mary K. Zeman
*Attorney, Agent, or Firm*—Townsend and Townsend and Crew LLP

[57] ABSTRACT

An approximately 37 kilodalton (kd) protein associated with grapevine leafroll disease infected plants is disclosed. The 37 kd protein is the coat protein for a grapevine leafroll-associated virus designated GLRaV-8. The grapevine virus-encoded 37 kd polypeptide is immunologically distinct from the approximately 36 kd proteins associated with GLRaV-4 or GLRaV-5 or the approximately 38 kd protein associated with GLRaV-1. The invention further provides a substantially pure antibody directed against the 37 kd virus-associated protein, a stable cell line capable of producing such a monoclonal antibody, and a method for assaying for a virus infection in Vitis species. The method involves detecting the presence of a 37 kd polypeptide encoded by an RNA-containing plant virus using an antibody that does not react with a viral encoded polypeptide of ca. 38 kd.

14 Claims, 3 Drawing Sheets

GLRaV I

GLRaV IV

GLRaV II

MIXED IgG

ANTIBODIES AND PROTEINS USEFUL FOR ASSAYING VIRUS INFECTION IN GRAPE PLANTS

This application claims the benefit of U.S. Provisional Application No. 60/004,087 filed Sep. 21, 1995 and Provisional Application No. 60/019,916 filed Jun. 14, 1996.

BACKGROUND OF THE INVENTION

Grapevine leafroll disease is found everywhere grapevines are grown and, in economic terms, is one of the most important diseases in the grape industry. Grapevine leafroll disease is associated with reduced yield, delayed ripening, altered fruit pigmentation, and reduced accumulation of sugar.

Several graft transmissible viruses have been reported to be associated with leafroll disease including a potyvirus (GPV), different strains of closterovirus-like particles (GLRaV-1, 2b, 3, 4, 5), grapevine virus A (GVA), and an uncharacterized isometric virus. Closterovirus-like particles, designated as grapevine corky bark associated viruses (GCBaV), have also been reported in association with corky bark disease. Grapevine cultivars often carry mixed infections of unrelated GLRaV (grape leafroll-associated viruses) and GCBaV.

Because of the destructive effects of leafroll disease, it is necessary to screen plants for the presence of leafroll disease associated-viruses, particularly before carrying out procedures such as bench-grafting, budding and varietal conversion which may spread the disease from one plant to another. Presently, diagnosis of infection by leafroll disease-associated viruses is done by biological indexing and ELISA tests. Biological indexing utilizes grape selections, called "indicator" varieties, which are especially sensitive to particular virus diseases. In an indexing test, buds from the grape selection being tested are grafted to potted vines of the indicator variety. The grafted plants are then grown in a field plot: if the tested selection has leafroll disease, the indicator vines will develop symptoms in approximately two years. Indexing is not a practical diagnostic tool for use on a commercial basis because of the length of time required for disease expression.

More rapid tests for leafroll disease (LD) associated viruses are immunological tests such as the Enzyme Linked Immunosorbent Assay (ELISA). However, because the known LD-associated viruses are distinct, ELISAs are specific for each virus and are, of course, available only for known viruses. Because antibodies are not available for all viruses a negative ELISA test may not be indicative of a virus-free plant. Other tests being developed, such as nucleic acid based tests, also are useful only for detecting known and characterized viruses.

Therefore, there is a need to identify new viruses associated with LD, and for improved assays for LD-associated viruses, especially assays directed to heretofore uncharacterized viruses. Molecular and immunological probes for detection of grapevine leafroll associated viruses will allow economical and reliable testing of grapevine nursery material and elimination of viruses from nursery stock.

SUMMARY OF THE INVENTION

The present invention provides a novel 37 kilodalton (kd) protein associated with grapevine leafroll disease infected plants. The protein is the coat protein for a grapevine leafroll-associated virus designated GLRaV-8. Specifically, the invention provides a substantially pure grapevine virus-encoded polypeptide having a molecular weight of approximately 37 kd, which is not reactive with antibodies directed against the approximately 36 kd proteins associated with GLRaV-4 or GLRaV-5, or the approximately 38 kd protein associated with GLRaV-1.

The invention further provides a substantially pure antibody directed against the 37 kd virus-associated protein, wherein the antibody does not react with a viral encoded polypeptide of ca. 38 kd associated with GLRaV-1 or the approximately 36 kd proteins associated with GLRaV-4 or GLRaV-5. A stable cell line capable of producing a monoclonal antibody that specifically binds the 37 kd polypeptide is also provided. It is also a part of this invention that the above antibody can be added artificially to a mixture of different GLRaV specific antibodies in an aliquot amount to provide a predetermined concentration to maximize their efficient use in the immunoassays described here.

The invention further provides a method for assaying for a virus infection in Vitis species comprising detecting the presence of a 37 kd polypeptide encoded by an RNA-containing plant virus using an antibody that does not react with a viral encoded polypeptide of ca. 38 kd. The antibody may be monoclonal or polyclonal. In one preferred embodiment the assay is an ELISA and in a second preferred embodiment the assay is a Western blot assay.

In addition the invention provides a kit which is useful for identifying GLRaV infected plants and which contains the 37 kd protein.

DETAILED DESCRIPTION OF THE INVENTION

A. Definitions

Vitis

Figure 1A:
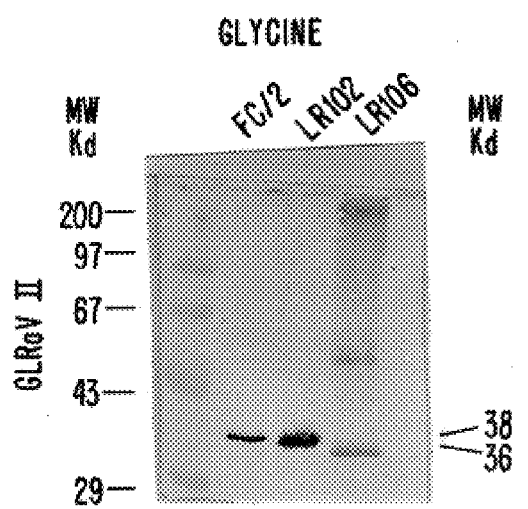
FIG. 1 shows Western blots of Tricine-SDS-PAGE (Tricine) or Laemmli (Glycine) gels in which purified virus from FC/2, LR102, and LR106 cultivars are stained with antibodies directed against specific GLRaV capsid proteins.
Figure 1D:
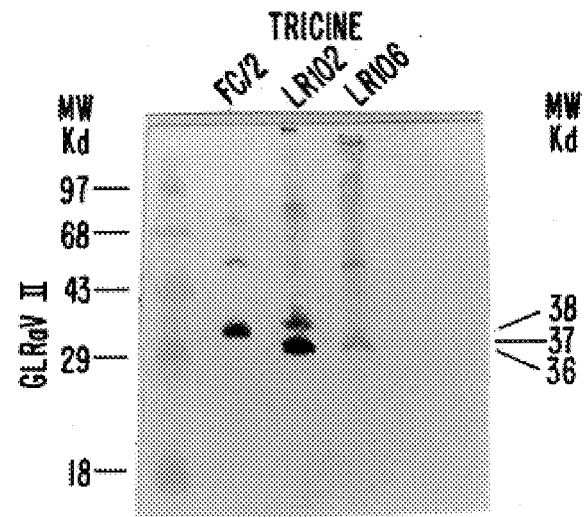
Figure 1B:
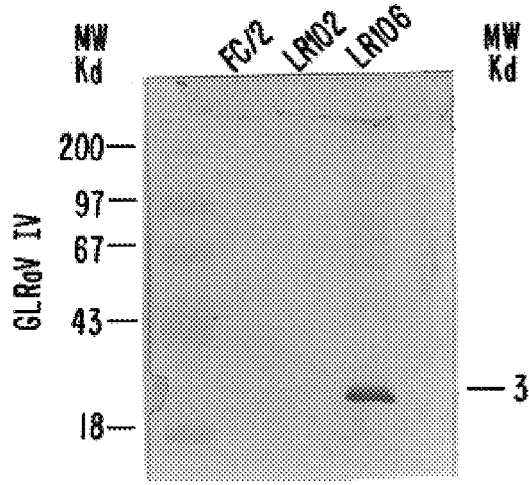
Figure 1E:
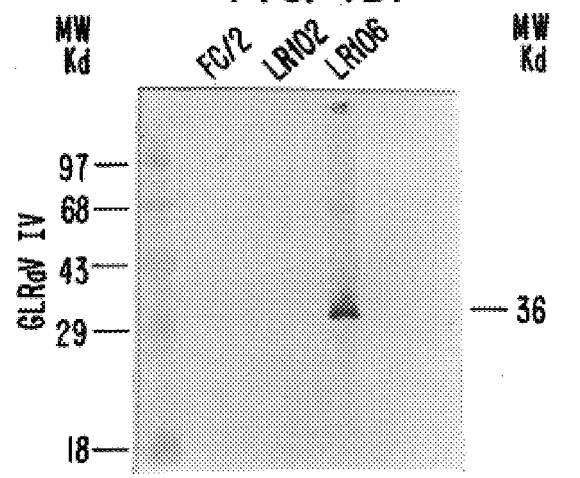
Figure 1C:
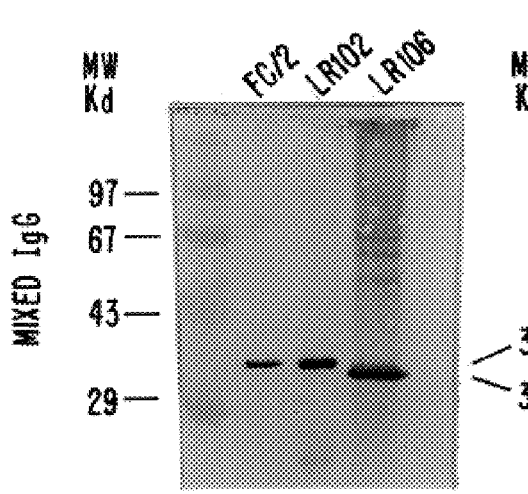
Figure 1F:
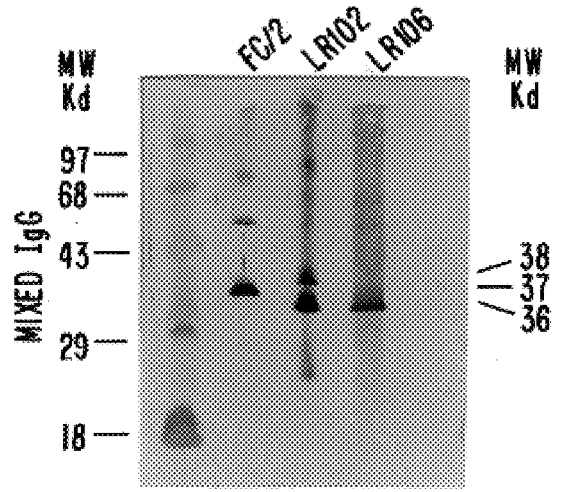
Figure 2A:
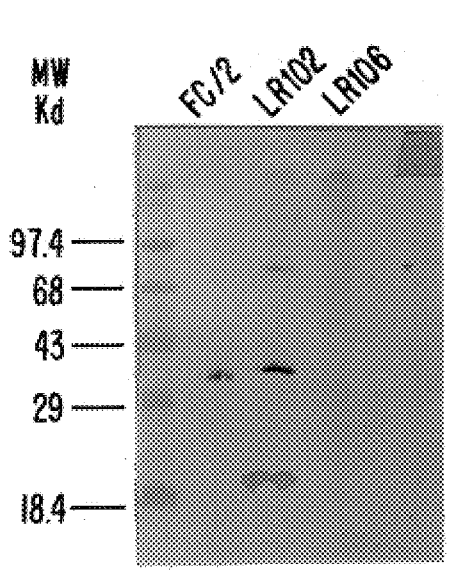
FIG. 2 shows Western blots of Tricine-SDS-PAGE gels in which purified virus from FC/2, LR102, and LR106 cultivars are stained with antibodies directed against specific GLRaV capsid proteins.
Figure 2C:
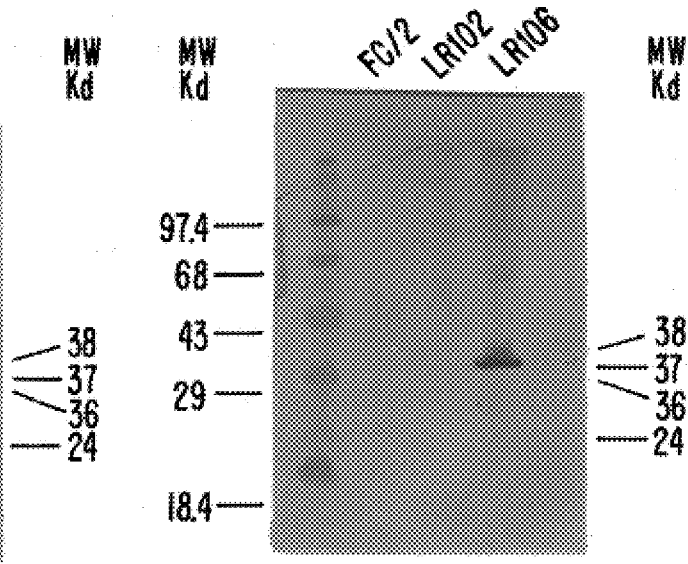
Figure 2B:
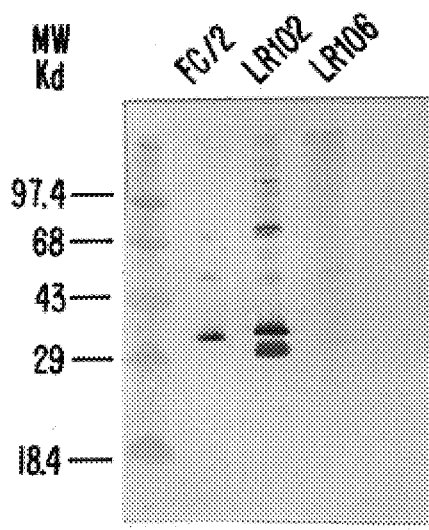
Figure 2D:
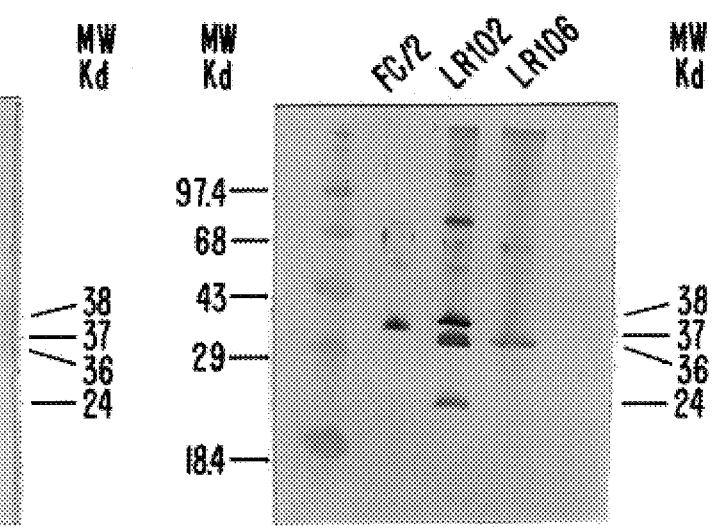

The production of wine, table grapes and raisins is based primarily on traditional cultivars of *Vitis vinifera*, of which approximately 10,000 are known. Some well known cultivars are listed in Mullins et al., *Biology of the Grapevine*, Cambridge (1994), e.g. at pages 27–36. Other agriculturally important Vitis species include *V. rupestris, V. riparia, V. berlandieti, V. candicans, V. cinerea, V. labrusca*. The products of crosses between these species (e.g., as described in Mullins et al., supra, at page 30, Table 2.6) are also agriculturally important and, as used herein, the term "Vitis" encompasses such products. Another important species of grape is *Muscadinia rotundifolia*, which can also be crossed with Vitis species.

Antibody

As used herein, "antibody, " "immunoglobulin, " or "antibody peptide(s)" refers to antibodies, monoclonal antibodies, to an entire immunoglobulin or antibody or any functional fragment of an immunoglobulin molecule which specifically binds to the 37 kd virus-associated protein disclosed herein. Examples of such peptides include complete antibody molecules, antibody fragments, such as Fab, F(ab')$_2$, complementarity determining regions (CDRs), V$_L$ (light chain variable region), V$_H$ (heavy chain variable region), and any combination of those or any other functional portion of an antibody peptide.

RNA-containing plant viruses

Various closterovirus-like particles have been described in association with different types of leafroll and corky bark diseases. Because Koch's postulates have not been completed with the viruses causing these diseases, the causal agents are referred to as grapevine leafroll associated (GLRaV) and grapevine corky bark associated (GCBaV) viruses. As used herein, a protein that is not encoded by uninfected Vitis plants, such as the Vitis riparia Gloire or Kober 5BB cultivars, and which is found in the purified virus fraction obtained from the LR102 cultivar is considered to be a virus-associated protein. Such a virus-associated protein is presumed to be a capsid protein of an RNA-containing plant virus. *Vitis riparia* Gloire or Kober 5BB cultivars as well as other grape cultivars are available from the Foundation Plant material Service (FPMS), University of California, Davis, Calif. and from the Saanichton Quarantine Station, Sydney, British Columbia, Canada.

Examples of RNA-containing plant viruses in grape include grapevine leafroll associated viruses, grapevine virus A, grapevine virus B, and grapevine corky bark associated viruses. A virus that infects a grape plant may also be referred to as a grapevine plant virus.

GLRaV-8 & 37 kd virus-associated protein

In accordance with current convention, GLRaV strains previously designated by a Roman numeral are herein designated by, and identical to, their Arabic numeric equivalent with a single exception. The exception relates to applicants' previous designation of their new viral strain as GLRaV VI. The GLRaV isolate designation GLRaV-8 is, for purposes of the present invention only, synonymous with the isolate originally designated GLRaV VI in an earlier provisional application. The isolate GLRaV-6 is now used to refer to an isolate of Chasselas cultivar as described in Boscia et al., *Vitis* 34(3):171–175 (1995) which is distinct from the isolate GLRaV-VI as disclosed herein. Choueiri et al. (*Vitis,* 35(2):91–93 (1996)) disclose a viral strain, designated as GLRaV-7, which is immunologically distinct from GLRaV-8.

The 37 kd virus-associated protein, as is disclosed herein, may be purified from the virally-infected grapevine cultivar "LR 102." LR 102 is publicly available from the "U.C Davis Grapevine Virus Collection" (see Golino, D.A., (1992) *Am. J. Enol. Vitic.*, 43:200–205). According to the terminology used herein, the 37 kd protein is a capsid protein for a virus referred to as grapevine leafroll-associated virus 8 (GLRaV-8). The grape leafroll associated virus designated GLRaV-8, strain designation LR102, was deposited on Apr. 14, 1998, at the American Type Culture Collection (ATCC), 10801 University Blvd., Mannasas, Va. 20110. The ATCC accession number is ATCC 209779.

It is well known that molecular weights determined by gel electrophoresis are approximate and their values depend on the method and conditions of electrophoresis. The 37 kd protein disclosed herein migrates at an apparent molecular weight of approximately 37,000 (e.g., 36,000 to 37,000) in 8% Tricine-SDS-PAGE (i.e., a "Tricine gel"). In a standard Tricine gel the protein sample is prepared in Laemmli loading buffer (Laemmli, U.K. (1970) *Nature* 227:680–685) and loaded onto a 4% stacking gel. The gel is run using a lower chamber (anode) buffer of 0.1 M Tris, pH 8.9 and an upper chamber (cathode) buffer of 0.1 M Tris, 0.1 M Tricine, 0.1% SDS, pH 8.25. Running conditions are 30 minutes at 40 volts, allowing the entire sample to enter the separating gel, at which time the voltage is increased to approximately 75–85 volts (V) and the gel run until the proteins have migrated an adequate distance (e.g., as assessed by migration of the loading dye). Buffers are changed as necessary (e.g., to maintain the proper pH.) Under these or similar conditions the 37 kd protein has slightly greater apparent mobility than the ca. 38 kd capsid protein of GLRaV-1. The 38 kd protein of GLRaV-1 has also been referred to as 39 kd (Zimmermann et al., 1990, *J. Phytopathology* 130, 205–218] and 38.8 kd (Gugerli et al., 1984, Rev. *Suisse Vitic. Arbotic. Hortic.* 16:299–304).

The 37 kd protein may also be visualized after electrophoresis on a Tris-Glycine SDS-PAGE gel (Laemmli, (1970) supra). When run on a "Laemmli gel" the 37kd protein has slightly greater apparent mobility than the ca. 38 kd capsid protein of GLRaV-1 and slightly less apparent mobility than the 36 kd capsid protein of GLRaV-4.

"Viral associated" or "viral encoded" means that the protein is detectable in the host infected with the viral pathogen. Its genetic origin is not important.

Substantially pure

The terms "substantially pure," "isolated," and "substantially homogenous, " are used interchangeably and describe a protein or peptide which has been separated from components that naturally accompany it. Typically, a monomeric protein is substantially pure when at least about 85 to 100% of a sample exhibits a single polypeptide backbone. Minor variants or chemical modifications typically share the same polypeptide sequence. A substantially pure protein will typically comprise about 85 to 100% (w/w) of a protein sample, more usually about 95%, and preferably will be over about 99% pure. Protein purity or homogeneity can be indicated by a number of means well known in the art, such as polyacrylamide gel electrophoresis of a protein sample, followed by visualizing a single polypeptide band on a polyacrylamide gel upon staining. "Staining" refers to reacting an antibody with a peptide and visualizing the antibody using a labeled secondary antibody (e.g., conjugated to alkaline phosphatase). For certain purposes higher resolution can be provided by using high performance liquid chromatography (HPLC) or a similar means for purification.

A GLRaV-8 protein is substantially free of naturally-associated components when it is separated from the native contaminants which accompany it in its natural state. Thus, a polypeptide that is chemically synthesized or synthesized in a cellular system different from the cell in which it naturally originates will be substantially free from its naturally-associated components.

Substantially free

The term "substantially free," in the context of solutions of antibodies, refers to solution in which the omitted antibodies are absent or present in concentrations that are not detectable given the limits of detection or sensitivity for a particular assay, and thus the term is relative.

B. Methods for Purification of GLRaV-8

Purified GLRaV-8 serves as a source of antigen for raising polyclonal or novel monoclonal antibodies, and for use as a positive control when assaying for the presence of virus or a virus-associated peptide. In addition, the purified protein is useful for determining the amino acid sequence of GLRaV-8 protein, which allows the design of oligonucleotide primers useful for cDNA cloning and synthesis. In a preferred embodiment the virus may be purified according to one of the methods described below.

i) Source of Materials

A preferred source of GLRaV-8 is the grapevine cultivar LR102. A preferred source of GLRaV-1 is the French Colombard (FC/2) cultivar. These and other useful cultivars are publicly available, e.g. from the "U.C. Davis Grapevine Virus Collection" (see Golino, D. A., (1992) *Am. J. Enol. Vitic.*, 43:200–205); the Foundation Plant Material Service (FPMS) at the University of California, Davis, Calif.

ii) Virus Purification

Virus may be purified according to standard methods for closterovirus purification. In a preferred embodiment the method of Hu et al. (1990a) *J. Phytopathology* 128:1–14, which is incorporated herein by reference, is used. In a second preferred embodiment the method of Zee et al. (1987) *Phytopathology* 77, 1427–1434, which is incorporated herein by reference, is used. In a particularly preferred embodiment, virus is purified according to the following protocol:

About seventy-two grams (g) of mature stems and petioles are harvested fresh or stored frozen at −80° C., powdered in liquid nitrogen in a Lab Mill (Aldrich, Cat. # Z15649–3) and mixed with 360 ml of Virus Extraction Buffer (VEB). VEB is 0.5 M Tris, pH 8.5, 5% Triton-X-100, 4% Polyclar (Serva), 0.2% β-mercaptoethanol and 0.5% sodium sulfite. The ground tissue/VEB mixture is transferred to centrifuge bottles and spun at 5000 rpm for 10 minutes in a Beckman JA 10 rotor (or an equivalent centrifugation speed). The resulting supernatant is filtered on ice through a layer of Miracloth (Calbiochem) into a beaker. Virus is purified from the supernatant as described below. If desired, additional virus may also be obtained from back extractions of the pellets by resuspending the pellets in 200 ml of 0.5 M Tris, pH 8.5, and stirring in the cold for 2 hours. The resuspended pellet is then transferred to centrifuge bottles and spun at 5000 rpm for 10 minutes in a Beckman JA 10 rotor (or an equivalent centrifugation) and the resulting supernatant filtered on ice through a layer of Miracloth into a beaker.

To concentrate virus from the supernatant(s), 45–50 ml of supernatant is transferred into a Beckman Ti 45 bottle. A 10–12 ml sucrose pad (20% sucrose in 0.1 M Tris pH 8.0) is underlaid and the samples are centrifuged for 2 h at 30,000 rpm at 4° C. in a Beckman Ti 45 rotor. The resulting supernatant is discarded and the pellets are resuspended in 6–12 mls of Virus Resuspension Buffer (VRB) by stirring overnight at 4° C.

The virus suspension is then transferred into a conical tube and allowed to sit in the cold overnight so that plant debris sediments to the bottom of the tube. The supernatant is recovered and the sediment is washed 2 times with 0.5 ml VRB. The supernatants from the washed sediments are combined with the virus suspension and transferred to a Ti 70.1 centrifuge tube and 1 ml of a 20% sucrose solution is underlaid as described above. The sample is then centrifuged at 40,000 rpm for 2.5 h at 4° C. in a Beckman Ti 70 rotor. The resulting pellets are resuspended in approximately 1.5 ml VRB and transferred to a 2.0 ml microcentrifuge tube with a micro stirring bar. The virus is resuspended by stirring at 4° C. overnight.

The following day the stirring bar is removed and the virus is allowed to freeze-thaw (e.g., −20° C. for 1 hr, followed by 0.5 h at room temperature) and the debris sedimented by spinning at 3,000 rpm for 3 min in a microcentrifuge. The sediment is washed in 100–200 μl VRB and the virus-containing supernatants are combined. This virus preparation may be frozen and stored at −80° C. with or without the addition of 5% ethylene glycol.

One of skill will recognize that there are numerous variations of this protocol that will be as, or more, useful for preparation of virus and that buffers, centrifugation conditions, and other purification parameters may be optimized or varied for convenience.

C. Methods for Purification of the 37 kd GLRaV-8 Associated Protein.

Having prepared purified or partially purified GLRaV-8 virus it is possible to prepare a substantially pure preparation of the 37 kd viral-associated protein. Although numerous methods and strategies for protein purification are known in the art it will be most convenient to purify the 37 kd protein by either (i) electrophoresis using a Tricine-SDS-polyacrylamide gel (Tricine-SDS-PAGE) or (ii) affinity chromatography. Each of these methods will be described in turn.

i) Electrophoresis

The viral coat proteins of GLRaV-8 isolated from LR102 cultivar are separated by electrophoresis using an 8% Tricine-sodium dodecyl sulfate-polyacrylamide gel (Tricine-SDS-PAGE) (Schagger and Von Jagow, 1987, *Analytical Biochemistry* 166, 368–379). The Tricine system is preferred over alternative electrophoretic methods such as the "Glycine-SDS-PAGE" system described by Laemmli, U.K. (1970) *Nature* 227:680–685 (which is incorporated herein by reference). This is because the Tricine system surprisingly resolves two polypeptides that react with polyclonal antibody directed against the anti-serum described by Boscia et al. raised against an isolate of GLRaV serotype 2 (1990, Characterization of grape leafroll associated closterovirus (GLRaV) serotype H and comparison with GLRaV V serotype III, *Phytopathology* 80:117). (Although the polyclonal antiserum of Boscia et al. (1990) is reported to be specific for a 36 kd polypeptide, this antiserum was determined to react with capsid proteins from several GLRaVs, presumably due to contaminating viruses in the viral preparation of Boscia et al.(1990)).

The area of the gel including the 37 kd polypeptides is excised (Schagger, H. (1994) *Applied Biochemistry and Biotechnology* 48:185–203) and eluted using an Elutetrap apparatus (Schleicher & Schuell, N.H.). The region of the gel containing the 37 kd protein is identified by Western blotting one lane of a slab gel and staining with the anti-GLRaV 2 polyclonal antibody to visualize the 37 kd and 38 kd viral protein bands. The Western blot is aligned with the remaining lane(s) of the gel and the region corresponding to the 37 kd band is excised. Alternatively, the slab gel or one lane of the gel can be stained (e.g., using silver stain) and the 37 kb band (along with any others present) can be identified by its relative mobility. To ensure purity the eluted protein is run on a second Tricine-SDS-PAGE and eluted a second time. The identity of the eluted protein is verified by Western blotting using anti-GLRaV 2 capsid polyclonal antibody and anti-GLRaV 1 capsid protein antibody. The peptide contained in the excised gel fragment is suitable for use in immunization or in peptide sequencing.

ii) Affinity Chromatography

The 37 kd protein may also be purified by affinity chromatography using an antibody (such as a monoclonal antibody) that specifically binds to the GLRaV-8 37 kd protein. The antibody may be covalently coupled to solid supports such as celluloses, polystyrene, polyacrylamide, cross-linked dextran, beaded agarose or controlled pore glass using bifunctional coupling agents that react with functional groups on the support and functional groups (i.e., reactive amino acid side chains) on the antibody molecule. See *Scientific Foundations of Clinical Biochemistry*, Vol. 1, pp. 202 et seq., (1978). The resulting monoclonal antibody-bearing solid phase is contacted with purified or partially purified virus under reducing conditions using pH, ionic strength, temperature and residence times that permit the 37 kd protein to bind to the immobilized antibody. The virus or protein is eluted from the column by passing an eluant that dissociates hydrogen bonds through the bed. Bases that lower the pH to below about 3 or NaCl solutions above about 2 M are commonly used elutants.

Methods for carrying out affinity chromatography using antibodies are well known in the literature (e.g., Harlow and Lane (1988) *Antibodies: A Laboratory Manual*, Cold Spring Harbor). Similarly, other methods for immunoaffinity purification of proteins (such as the 37 kd GLRaV-8 viral coat protein) are well known in the art and are described, for example, in Harlow and Lane, supra.

D. Production of Antibodies

Antibodies, either monoclonal or polyclonal, can be generated to the purified or partially purified 37 kd protein or peptide fragments in a variety of ways known to those skilled in the art including injection of antigen into animals, by hybridoma fusion, and by recombinant methods involving bacteria or phage systems (see Marks et al. (1992) *J. Biol. Chem.* 267:16007, Marks et al. (1992) *Biotechnology* 10:779; Lowman et al. (1991) *Biochem.* 30:10832; Lerner et al. (1992) *Science* 258:1313; each of which is incorporated herein by reference).

Antibodies may be produced by immunizing an appropriate vertebrate host, e.g., rabbits, goats and mice with the peptide itself or in conjunction with an adjuvant. Usually two or more immunizations will be involved, and the blood or spleen will be harvested a few days after the last injection. For polyclonal antisera, the immunoglobulins may be precipitated, isolated and purified, including affinity purification. For monoclonal antibodies, the splenocytes normally will be fused with an immortalized lymphocyte, e.g., a myeloid line, under selective conditions for hybridomas. The hybridomas may then be cloned under limiting dilution conditions and their supernatants screened for antibodies having the desired specificity. Techniques for producing antibodies are well known in the literature and are exemplified by U.S. Pat. Nos. 4,381,292, 4,451,570, and 4,618,577, and are described in Harlow and Lane (1988), supra. Production of monoclonal antibodies directed against a GLRaV are described in Hu et al. (1990), *Phytopathology* 80:920–925. Typically, an antibody directed against the 37 kd virus-associated protein will have a binding affinity of at least $1 \times 10^7$ M$^{-1}$.

One use of such antibodies is to screen cDNA expression libraries for identifying clones containing cDNA inserts which encode the 37 kd protein or structurally-related, immuno-crossreactive proteins. Such screening of cDNA expression libraries is well known in the art, and is further described in Young et al., 1983, *Proc. Natl. Acad. Sci. U.S.A.* 80:1194–1198, which is incorporated herein by reference, as well as other published sources. Another use of these antibodies is for use in affinity chromatography for purification of GLRaV-8 or the 37 kd protein. These proteins are also useful for assaying for GLRaV-8 infection.

E. Assays for Viral Infection

A number of immunologically based assays may be carried out to identify plants infected with GLRaV-8. Although assays are described in some detail below, one of skill will understand that, provided with a monoclonal or polyclonal antibody that recognizes a plant virus-encoded protein such as those disclosed herein, a variety of assay formats are available. Assay formats are well known in the literature and are described, for example, in Harlow and Lane, supra. Descriptions of assay methods for ELISA, Immunogold labeling, Western Blotting, and Dot-immunoblotting are also found in Hu et al. (1990), supra. Other methods, such as immunosorbent electron microscopy (ISEM) are also well known to those of skill (see, e.g., Pietersen, G. and Kasdorf, G. (1993) *Extended Abstracts, 11th Meeting of the International Council for the Study of Viruses and Virus Diseases of the Grapevine*, page 140).

i) Western Blot Immunoassay

Western blot assays are described generally in Harlow and Lane, supra and in Hu et al. (1990a,b), supra. According to this method the viral proteins (and other proteins in the virus preparation) are separated by gel electrophoresis and transferred to a solid phase (i.e., a membrane such as nitrocellulose). The immobilized antigen is subsequently reacted with an antibody and detection system (e.g., an alkaline phosphatase-conjugated second antibody).

In a preferred protocol plants are screened for the presence of GLRaV-8 by (i) concentrating virus from the grapevine cultivars to be tested, (ii) denaturing the viral preparation, (iii) subjecting the denatured proteins to polyacrylamide gel electrophoresis to separate the 37 kd GLRaV-8 peptide from other viral and plant proteins, (iv) and detection of the 37 kd protein, if present, using monoclonal or polyclonal antibodies. As will be apparent to those of skill, it will be advantageous to include appropriate negative and positive control materials (such as substantially purified 37 kd antigen or GLRaV-8 virus) in the assay.

ii) ELISA

Enzyme Linked Immuno-Sorbent Assays (ELISA) are described generally in Harlow and Lane, supra and in Hu et al., (1990a,b). The assay involves the reaction of a viral component (e.g., the 37 kd protein) with an antibody. In one embodiment the plant tissue is ground and reacted to the antibody that has been coated onto a solid phase such as a test plate. If the virus is present in the sample, an enzyme-labeled specific antibody will bind to the antibody-virus complex, and it will be detected by an enzyme substrate reaction that produces a color reaction. A preferred method of ELISA analysis is the double antibody sandwich (DAS) described by Hu et al., (1990) and by Gugerli et al. (1984) *Rev. Suisse Vitic. Arboric. Hortic.* 16:299–304, which are incorporated herein by reference. It will be apparent to those of skill that in an ELISA or any other type of assay it will sometimes be desirable to measure for the presence of more than one viral capsid protein in a single reaction, for example by mixing two or more antibodies with different specificities and assaying for peptides that react with any of the antibodies.

iii) Nucleic Acid Based Methods

Plant viruses infecting grapevine are composed of a ribonucleic acid (RNA) and a protective capsid protein. The methods described above are focused on immunological detection of the capsid protein for the detection of the virus. By recombinant DNA technology it is possible to produce probes that directly or indirectly hybridize to the viral RNA (or its complement) and which can be used in assays for the detection of a particular virus. The polymerase chain reaction (PCR) and immunocapture-PCR (IC-PCR) techniques allow the amplification of fragments of viral nucleic acids which might be present in very low amounts. To detect GLRaV-8 by nucleic acid hybridization, the 37 kd protein (i.e., the capsid protein of GLRaV-8) is sequenced or, alternatively, the viral genomic RNA may be isolated from purified virus and directly cloned and/or sequenced. Using either the cloned nucleic acid as a hybridization probe, using sequence information derived from the clone, or by designing primers based on the amino acid sequence of the 37 kd protein, nucleic acid hybridization and/or PCR may be used to assay for the presence of the virus.

F. Kits

A kit for detecting a grapevine plant virus may, depending on the assay format, include monoclonal and/or polyclonal antibodies specific for the 37 kd protein of GLRaV-8 as well as substantially purified 37 kd protein, e.g., for use as a positive control.

Although the present invention has been described in some detail by way of illustration and example for purposes of clarity of understanding, it will be obvious that certain changes and modifications may be practiced within the scope of the appended claims.

EXAMPLES

Example 1

The 37 kd Protein Associated with LR102 is Serologically Distinct from other GLRaVs.

Table I shows the reported capsid protein sizes for GLRaV 1, 2, 2b, 3, 4, 5, GVA, and GCBaV.

TABLE 1

| Protein Size (kd) | Corresponding Virus | Ref |
|---|---|---|
| 37 | GLRaV-8 | |
| 38 | GLRaV-1 (isolated from LR 102) | 1 & 2 |
| 39 (ref. 1) | | |
| 38.8 (ref. 2) | | |
| 24 | GLRaV-2 | 1 |
| 26.5 | GLRaV-2b | 2 |
| 43 (ref. 1) | GLRaV-3 | 1, 2, & 3 |
| 44.3 (ref. 2) | | |
| 36 (ref. 1) | GLRaV-4 | 1 & 2 |
| 34.7 (ref. 2) | | |
| 35.6 | GLRaV-5 | 2 |
| 25.1 | GVA | 2 |
| 24 | GCBaV | 4 |

1. Zimmermann et al. (1990) Phytopathology 130,205–218 (GLRV-1 = GLRaV-1; GLRA-2 = GLRaV-2; GLRA3 = GLRaV-3; GLRA-4 = GLRaV-4).
2. Gugerli, P. and Ramel, M-E (1993) Extended Abstracts, 11th Meeting of the International Council for the Study of Viruses and Virus Diseases of the Grapevine, pages 23–24.
3. Hu et al. (1990) Phytopathology 80:920–925.
4. Namba et al. (1991) Phytopathology 81:964–970.

To demonstrate that the 37 kd GLRaV-8 is serologically distinct from previously identified GLRaV proteins, virus was concentrated from LR102 as described in Section B(i)(b), supra and Western blot assays were carried out. The concentrated viral fraction from LR102 was subjected to electrophoresis on a 8% Tricine-SDS-PAGE essentially as described supra. After gel electrophoresis, the resolved proteins were electrophoretically blotted to nitrocellulose and stained with various polyclonal and monoclonal immunoglobulins according to standard procedures (e.g., as described in Harlow and Lane, supra). Anti-GLRaV capsid protein antibodies were obtained as follows: GLRaV-1 monoclonal antisera was purchased from BIOREBA AG (Basel, Switzerland), GLRaV-2b monoclonal antisera were provided by Dr. P. Gugerli (Nyon Agricultural Experimental Station, Switzerland); monoclonal GLRaV-3 was obtained from Dr. D. Gonsalves (New York State Experimental Station, Geneva, N.Y.). A polyclonal antisera reported to be raised against GLRaV-2 was obtained from Dr. Dennis Gonsalves (Boscia et al. (1990) Phytopathology 80:117). This polyclonal antibody reacts with proteins from GLRaV-1, 2b, 2 (i.e., GLRA-2; Zimmerman et al., supra) and IV viral isolates. "Mixed IgG" is a mixture of four antisera: the polyclonal described by Boscia et al., (1990) supra, an anti-GLRaV-4 polyclonal (Hu et al., (1990),J. Phytopathology 128:1–14) and a anti-GLRaV-3 monoclonal (Hu et al., (1990), Phytopathology 80:920–925), all obtained from Dr. D. Gonsalves, plus the 24 kd-RSI polyclonal antisera produced at Agritope, Inc. which was raised against grapevine isolates showing rootstock-scion incompatibility (RSI) symptoms.

The results of these experiments are summarized in FIGS. 1 and 2. In each of Panels A-F, purified viral fractions from cultivars FC/2, LR102, and LR106 were separated by electrophoresis and transferred to nitrocellulose. Panels A-E show the results of electrophoresis on a Laemmli gel system and Panels D-F show the results of electrophoresis on a Tricine-SDS-PAGE system.

Panels A and D of FIG. 1 and Panel B of FIG. 2 show a Western blot stained with polyclonal antibody directed against the 24 kd capsid protein of GLRaV-2. This polyclonal antibody also recognizes the 38 kd protein of GLRaV-1 (see the staining of this band in the FC/2 cultivar known to be infected with GLRaV-1) and the 36 kd protein of GLRaV-4 (see the staining of this band in the LR106 cultivar known to be infected with GLRaV-4) and the 24 kd proteins associated with GCBaV, GLRaV-2 (Zimmerman et al., supra), GLRaV-2b, and RSI. In the glycine gel a single band from the LR102 extract reacts with this antibody; however, the same extract in a Tricine gel resolves into two bands, one of 38 kd which is the GLRaV-1 capsid protein and one of approximately 37 kd which is the GLRaV-8 protein.

Panels B and E of FIG. 1 and Panel C of FIG. 2 show a Western Blot stained with antibody directed against the 36 kd capsid protein of GLRaV-4. This antibody does not recognize the 37 kd protein of GLRaV-8, demonstrating that GLRaV-8 is serologically distinct from GLRaV-4.

Panels C and F of FIG. 1 and Panel D of FIG. 2 show staining with a mixture of polyclonal and monoclonal antibodies selected to stain all known GLRaVs plus GLRaV-8.

Panel A of FIG. 2 shows staining with GLRaV-1 monoclonal, indicating that the 37 kd protein is serologically distinct from the 38 kd GLRaV-1 protein.

In addition, Western Blots have been carried out which demonstrate that monoclonal antibody specific for GLRaV-5 does not react with the LR102 purified virus preparation.

The results, taken together, indicate that the 37 kd polypeptide associated with LR 102 (i.e., the GLRaV-8 coat protein) is serologically distinct from known GLRaVs.

Example 2

Production of Polyclonal Antibodies Directed Against the GLRaV-8 Polypeptide

For production of polyclonal antibodies directed against the 37 kd protein associated with GLRaV-8, protein is purified from the LR 102 grapevine isolate. The identity of the purified protein was verified by Tricine-SDS-PAGE and Western blotting using GLRaV-1 monoclonal (no reactivity) and GLRaV-2 polyclonal antisera (staining of a 37 kd polypeptide) prior to immunization of mice. A single protein band of 37 kd was observed in all purified protein preparations of LR 102.

Grapevine leafroll associated Virus 8 was isolated from LR 102 diseased grapevine material following the protocol described in detail in Section B(ii), supra. Crude virus preparations were mixed with Laemmli sample buffer at a final concentration of 0.0625 M Tris-HCl pH 6.8, 2% SDS, 10% Glycerol, 5% β-mercaptoethanol, 0.001% bromophenol blue, and loaded onto 1 mm thick SDS-Tricine-preparative PAGE. The gel was run for 30 minutes at 40 V (until all the preparation moved into the separating gel), the voltage was increased to 75 V. The anode buffer was changed every 1.5 hr. After running for 3 hr the voltage was increased to 85 V. The gels were run for a total of 6 hr and 15 minutes. The lanes on the edges of the gels were sliced and transferred to nitrocellulose and processed using the Western blot assay (WB) to locate the 37 kd polypeptide. After development, the WB strips were aligned with the preparative PAGE and a the slice of gel containing the 37 kd protein was excised and eluted using an Elutetrap apparatus. The eluted protein preparation was run in a second dimension of 8% SDS-Tricine-PAGE.

Figure 3A:
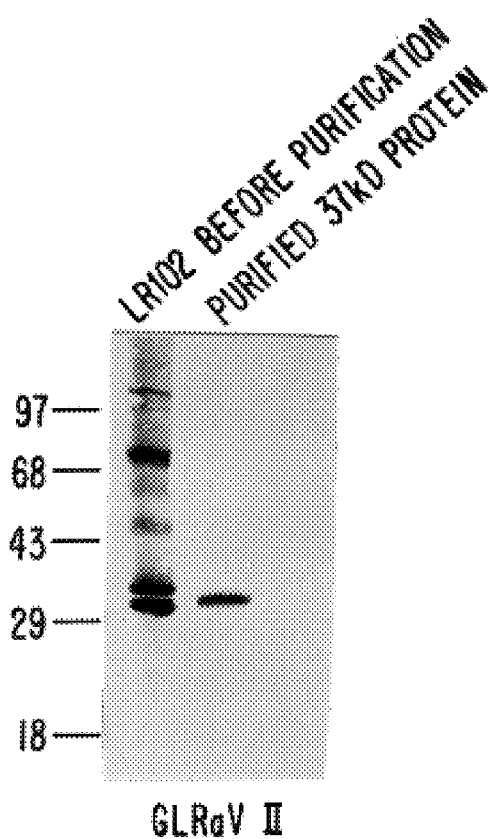
FIG. 3 shows the purified 37 kd protein and reactivity with anti-GLRaV-2 polyclonal IgG and anti-GLRaV-1 mAb.
Figure 3B:
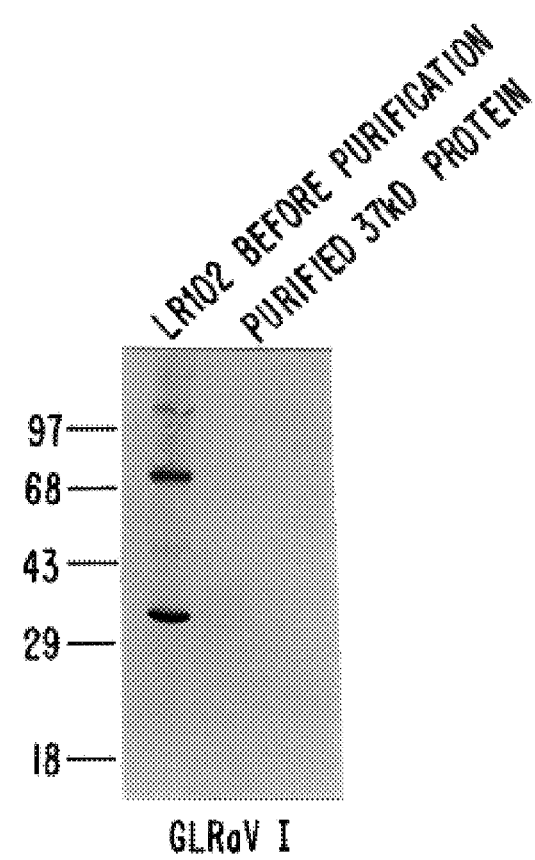

The eluted proteins were analyzed using the SDS-Tricine PAGE and WB using GLRaV-2 polyclonal, GLRaV-1, and GLRaV-5 monoclonal antibodies. A single polypeptide of approximately 37 kd was reactive to the GLRaV-2 polyclonal antibodies and did not react to GLRaV-1 and GLRaV-5 monoclonal antibodies. See FIG. 3, showing the reactivity of gel purified 37 kd polypeptide to GLRaV-1 and GLRaV-2 antibodies. To produce antiserum, mice were pre-bled and tested for their immunogenicity to healthy grapevine extracts. The mice with the lowest reactivity to healthy grapevine extracts were chosen to be immunized with gel purified 37 kd protein or affinity purified GLRaV-8. All protein extracts were emulsified using complete Freunds adjuvant prior to primary immunizations (Harlow and Lane, (1988), supra).

In production of antiserum, booster injections with incomplete Freunds adjuvant are included to increase the titer of the polyclonal antisera to the 37 kd viral polypeptides. Mouse bleedings are tested using the Western blot assay to determine the reactivity of antisera to the viral protein extracts.

The reactivity of the antisera is verified by Western blot immunoassays using cut nitrocellulose strips of SDS-PAGE separated and electroblotted healthy, FC/2 (no reactivity expected) and LR 102 protein extracts. The antisera specific to the 37 kd polypeptide is expected to react to a single polypeptide in LR 102 preparations.

Example 3
Production of Monoclonal Antibodies (mAbs) Directed Against the p37 Polypeptide The 37 kd polypeptide (p37) was purified from LR 102 virus preparations as described in Example 2. Three booster injections were necessary to increase the titer of the antibodies. The mice serum was tested using ELISA and western blot (WB) to determine its reactivity to different GLRaV isolates. The mice sera was reactive to the p37 polypeptide from LR 102 and the 36 kd polypeptide (p36) from LR 100 as determined by SDS-Tricine-PAGE. The splenocytes from the immunized mice were collected and fused with myeloma cells. Harlow and Lane, (1988), supra. The hybridoma cell lines were screened against different GLRaV isolates using both ELISA and the Western blot assay (Table 2).

TABLE 2

ELISA reactivity of cloned monoclonal antibodies

| Cell Line | LR 102 | LR 100 | LR106 | FC/2 | Healthy |
|---|---|---|---|---|---|
| 3F7 | neg | neg | neg | neg | neg |
| 5G5 | neg | neg | neg | neg | neg |
| 14F9 | pos++ | neg | neg | neg | neg |
| 15F1 | pos+++ | pos++ | neg | neg | neg |
| 19A12 | pos+++ | neg | neg | neg | neg |

TABLE 2-continued

Western Blot reactivity of cloned monoclonal antibodies

| Cell Line | LR 102 | LR 100 | LR 106 | FC/2 | Chasselas | Healthy |
|---|---|---|---|---|---|---|
| 3F7 | pos++ | pos+ | pos+ | neg | neg | neg |
| 5G5 | pos+++ | pos++ | neg | neg | neg | neg |
| 14F9 | pos+ | neg | neg | neg | neg | neg |
| 15F1 | pos+++ | pos++ | neg | neg | neg | neg |
| 19A12 | pos++ | neg | neg | neg | neg | neg |

LR 100 is a cultivar associated with GLRaV-5. LR 102 is a cultivar infected with GLRaV-8, GLRaV-1, and GLRaV-2. LR 106 is a cultivar infected with GLRaV-4. Chasselas is a cultivar infected with GLRaV-6. Boscia et al., Vitis 34(3) :171–175 (1995). FC/2 is a French Colombard cultivar infected with GLRaV-1. Healthy is the uninfected Vitis riparia Gloire cultivar. Signal strength is indicated as negative (neg), or positive (pos) in ascending level of strength from + to +++. For ELISA, a single "+" represented at least twice background. For western blots, a single "+" indicated a clear and distinct band.

The cell lines with the desired reactivities were cloned using the limiting dilution method. Harlow and Lane, (1988), supra The following cell lines have been cloned and tested by ELISA and western blot (WB) for reactivity to the 36, 37, and 38 kd viral proteins:

14F9: with ELISA and Western Blot reactivity limited to the 37 kd viral protein (GLRaV-8) which is associated with the LR 102 isolate only.

19A12: with ELISA and Western Blot reactivity limited to the 37 kd viral protein (GLRaV-8) which is associated with the LR 102 isolate only. The hybridoma cell line 19A12 was deposited according to the terms of the Budapest Treaty with the American Type Culture Collection (ATCC) of 12301 Parklawn Dr.; Rockville, Md. U.S.A. on Jun. 26, 1996 and assigned Accession No. HB-12134.

15FI: with WB and ELISA reactivity to the 37 kd viral protein (GLRaV-8) which is associated with LR 102, and to the 36 kd viral protein (GLRaV-5) which is associated with LR 100. 3F7: with WB reactivity to the 37 kd viral protein associated with LR 102 (GLRaV-8), the 36 kd viral protein associated with LR 100 (GLRaV-5), and reactivity to the 36 kd viral protein associated with LR 106 (GLRaV-4).

5G5: with WB reactivity to the 37 kd viral protein associated with LR 102 (GLRaV-8), and the 36 kd viral protein associated with LR 100 (GLRaV-5).

The data indicates that the approximately 36, 37 kd polypeptides share at least one epitope and the 37 kd protein (p37) associated with GLRaV-8 is clearly distinct from the capsid proteins of GLRaV-4 and -5. The GLRaV-4 antibodies were not able to detect the 37 kd polypeptides in WB presumably because epitopes in common were not available. The data also indicates that GLRaV isolate GLRaV-6, is distinct from GLRaV-8 (i.e., GLRaV VI).

In sum, hybridoma cell lines were obtained with mono specificity to p37, and with broad spectrum reactivity (p37 associated with LR102, p36 associated with LR 100 and LR 106; p37 associated with LR102 and p36 associated with LR 100). The fact that denatured antigens were used for the immunization did not affect the screening of hybridomas that were reactive to native or denatured proteins.

All publications and patents mentioned in this specification are herein incorporated by reference into the specification to the same extent as if each individual publication or patent was specifically and individually indicated to be incorporated herein by reference.

What is claimed is:

1. A method for assaying for a grapevine leafroll-associated virus 8 virus infection in a species of Vitis comprising:

(1) binding a viral encoded polypeptide with an antibody in a solution;
wherein the solution has an undetectable amount of antibodies that react with closteroviruses grapevine leafroll-associated virus 1, grapevine leafroll-associated virus 4, or grapevine leafroll-associated virus 5,
wherein the polypeptide migrates at an apparent molecular weight of about 37 kd in a 8% Tricine-sodium dodecyl sulfate-polyacrylamide gel;
wherein the virus encoding the polypeptide is an RNA-containing plant virus,
wherein the viral encoded polypeptide reacts with monoclonal antibodies produced by the hybridoma cell line 19A12, ATCC Accession No. HB-12134; and, (2) detecting the bound antibody.

2. The method of claim 1 wherein the antibody is a monoclonal antibody.

3. The method of claim 1 wherein the antibody is immobilized on a solid phase.

4. The method of claim 1 wherein the 37 kd protein is detected using an enzyme-linked immuno-sorbent assay (ELISA).

5. The method of claim 1 wherein the 37 kd protein is detected using a Western blot.

6. An isolated antibody that specifically binds to a polypeptide encoded by a grapevine plant virus wherein:

the polypeptide migrates at an apparent molecular weight of about 37 kd in a 8% Tricine-sodium dodecyl sulfate-polyacrylamide gel;

the antibody does not react with closteroviruses or grapevine leafroll-associated virus 1, or grapevine leafroll-associated virus 4, or grapevine leafroll-associated virus 5;

the polypeptide reacts with monoclonal antibodies produced by the hybridoma cell line 19A12, ATCC Accession No. HB-12134; and the polypeptide is the coat protein of an RNA-containing plant virus.

7. The isolated antibody of claim 6 wherein said antibody is a monoclonal antibody.

8. A stable cell line capable of producing the monoclonal antibody of claim 7.

9. An isolated grapevine virus polypeptide:

wherein the polypeptide migrates at an apparent molecular weight of about 37 kd in a 8% Tricine-sodium dodecyl sulfate-polyacrylamide gel;

wherein the polypeptide is not reactive with antibodies generated against or reactive with closteroviruses or grapevine leafroll-associated virus 1, or grapevine leafroll-associated virus 4, or grapevine leafroll-associated virus 5; and wherein the polypeptide reacts with monoclonal antibodies produced by the hybridoma cell line 19A12, ATCC Accession No. HB-12134.

10. A kit for detecting a grapevine plant virus comprising an antibody that specifically binds to a polypeptide encoded by a grapevine plant virus, wherein the antibody does not react with closteroviruses or grapevine leafroll-associated virus 1, or grapevine leafroll-associated virus 4, or grapevine leafroll-associated virus 5;

wherein the polypeptide migrates at an apparent molecular weight of about 37 kd in a 8% Tricine-sodium dodecyl sulfate-polyacrylamide gel; and, wherein the polypeptide reacts with a monoclonal antibody produced by the hybridoma cell line 19A12, ATCC Accession No. HB-12134.

11. An isolated viral polypeptide which migrates at an apparent molecular weight of about 37 kd in a 8% Tricine-sodium dodecyl sulfate-polyacrylamide gel, wherein said polypeptide is not reactive with antibodies generated against closteroviruses or grapevine leafroll-associated virus 1, or grapevine leafroll-associated virus 4, or grapevine leafroll-associated virus 5, prepared by a process comprising:

contacting a purified or partially purified closterovirus with an antibody having the same specificity as the isolated antibody of claim 6;

permitting the antibody to specifically bind to a viral protein;

immobilizing the antibody; and, eluting the viral polypeptide from the antibody.

12. An isolated viral polypeptide which migrates at an apparent molecular weight of about 37 kd in a 8% Tricine-sodium dodecyl sulfate-polyacrylamide gel, wherein said polypeptide is not reactive with antibodies generated against closterovirus or grapevine leafroll-associated virus 1, or grapevine leafroll-associated virus 4, or grapevine leafroll-associated virus 5, prepared by a process comprising:

separating grapevine leafroll-associated virus 8 coat protein virus polypeptides by gel electrophoresis using an 8% Tricine-sodium dodecyl sulfate-polyacrylamide gel;

excising an area of a gel including polypeptides with an apparent molecular weight of about 37 kd; and, eluting the excised polypeptides from the gel.

13. The kit of claim 10, further comprising a positive control, wherein the positive control is a grapevine virus polypeptide having the following properties:

(a) migrates at an apparent molecular weight of about 37 kd in a 8% Tricine-sodium dodecyl sulfate-polyacrylamide gel; is not reactive with antibodies generated against or reactive with closteroviruses grapevine leafroll-associated virus 1, grapevine leafroll-associated virus 4, or grapevine leafroll-associated virus 5; and reacts with monoclonal antibodies produced by the hybridoma cell line 19A12, ATCC Accession No. HB-12134; or (b) migrates at an apparent molecular weight of about 37 kd in a 8% Tricine-sodium dodecyl sulfate-polyacrylamide gel, is not reactive with antibodies generated against closteroviruses grapevine leafroll-associated virus 1, grapevine leafroll-associated virus 4, or grapevine leafroll-associated virus 5, and is prepared by a process comprising: contacting a purified or partially purified closterovirus with an antibody, permitting the antibody to specifically bind to a viral protein; immobilizing the antibody; and, eluting the viral polypeptide from the antibody, wherein the antibody specifically binds to a polypeptide encoded by a grapevine plant virus, wherein the polypeptide migrates at an apparent molecular weight of about 37 kd in a 8% Tricine-sodium dodecyl sulfate-polyacrylamide gel; the antibody does not react with closteroviruses grapevine leafroll-associated virus 1, grapevine leafroll-associated virus 4, or grapevine leafroll-associated virus 5; the polypeptide reacts with monoclonal antibodies produced by the hybridoma cell line 19A12, ATCC Accession No. HB-12134; and the polypeptide is the coat protein of an RNA-containing plant virus; or, (c) migrates at an apparent molecular weight of about 37 kd in a 8% Tricine-sodium dodecyl sulfate-polyacrylamide gel, is not reactive with antibodies generated against closterovirus grapevine leafroll-associated virus 1, grapevine leafroll-associated virus 4, or grapevine leafroll-associated virus 5, is prepared by a process comprising separating grapevine leafroll-associated virus 8 coat protein virus polypeptides by gel electrophoresis using an 8% Tricine-sodium dodecyl sulfate-polyacrylamide gel, excising an area of a gel including polypeptides with an apparent molecular weight of about 37 kd, and, eluting the excised polypeptides from the gel.

14. The kit of claim 10, wherein the antibody is a substantially pure antibody, which specifically binds to a polypeptide encoded by a grapevine plant virus, wherein the polypeptide migrates at an apparent molecular weight of about 37 kd in a 8% Tricine-sodium dodecyl sulfate-polyacrylamide gel; the antibody does not react with closteroviruses grapevine leafroll-associated virus 1, grapevine leafroll-associated virus 4, or grapevine leafroll-associated virus 5; the polypeptide reacts with monoclonal antibodies produced by the hybridoma cell line 19A2, ATCC Accession No. HB-12134; and the polypeptide is the coat protein of an RNA-containing plant virus.

* * * * *